United States Patent
Brzozowski et al.

(10) Patent No.: US 11,540,720 B2
(45) Date of Patent: Jan. 3, 2023

(54) METHODS, SOFTWARE AND SYSTEMS FOR IMAGING

(75) Inventors: Lukasz Brzozowski, Toronto (CA); Janis W. Richmond, Clarksville, MD (US); Richard L. Croft, Oakville (CA)

(73) Assignee: Stryker European Operations Limited, Carrigtwohill (IE)

(*) Notice: Subject to any disclaimer, the term of this patent is extended or adjusted under 35 U.S.C. 154(b) by 3261 days.

(21) Appl. No.: 14/379,290

(22) PCT Filed: Oct. 9, 2007
(Under 37 CFR 1.47)

(86) PCT No.: PCT/US2007/080847
§ 371 (c)(1),
(2), (4) Date: Sep. 28, 2015

(87) PCT Pub. No.: WO2008/070269
PCT Pub. Date: Jun. 12, 2008

(65) Prior Publication Data
US 2016/0038027 A1    Feb. 11, 2016

Related U.S. Application Data

(60) Provisional application No. 60/828,619, filed on Oct. 6, 2006.

(51) Int. Cl.
*A61B 5/00* (2006.01)
*A61K 49/00* (2006.01)
*A61B 18/00* (2006.01)

(52) U.S. Cl.
CPC .......... *A61B 5/0071* (2013.01); *A61B 5/0036* (2018.08); *A61B 5/0044* (2013.01); *A61B 5/0059* (2013.01); *A61B 5/0077* (2013.01); *A61K 49/0032* (2013.01); *A61B 2018/00351* (2013.01); *A61B 2018/00577* (2013.01); *A61B 2576/023* (2013.01)

(58) Field of Classification Search
CPC ... A61B 5/0071; A61B 5/0036; A61B 5/0044; A61B 5/0059; A61B 5/0077; A61B 2018/00351; A61B 2018/00577; A61B 2576/023; A61K 49/0032
See application file for complete search history.

(56) References Cited

U.S. PATENT DOCUMENTS

| | | | |
|---|---|---|---|
| 5,009,233 A * | 4/1991 | Petrohilos | A61B 5/1076 356/640 |
| 5,279,298 A | 1/1994 | Flower | |
| 5,699,798 A | 12/1997 | Hochman et al. | |
| 6,351,663 B1 | 2/2002 | Flower et al. | |
| 6,443,976 B1 | 9/2002 | Flower et al. | |
| 6,607,495 B1 * | 8/2003 | Skalak | A61B 5/411 600/573 |
| 6,840,933 B1 | 1/2005 | Pang et al. | |
| 6,915,154 B1 * | 7/2005 | Docherty | A61B 5/0275 600/431 |
| 6,944,493 B2 | 9/2005 | Alam et al. | |
| 2006/0239921 A1 * | 10/2006 | Mangat | A61K 49/0032 424/9.6 |

* cited by examiner

*Primary Examiner* — Peter Luong
(74) *Attorney, Agent, or Firm* — Morrison & Foerster LLP

(57) ABSTRACT

The invention provides methods and systems for imaging.

12 Claims, 4 Drawing Sheets

METHODS, SOFTWARE AND SYSTEMS FOR IMAGING

CROSS-REFERENCE TO RELATED APPLICATIONS

This application is filed under 35 U.S.C. 371 as a U.S. national phase application of PCT/US07/80847, having an international filing date of Oct. 9, 2007, which claims priority to U.S. Provisional Application No. 60/828,619 filed Oct. 6, 2006, both of which i are incorporated by reference herein.

FIELD OF THE INVENTION

The invention relates to the field of medical imaging.

BACKGROUND OF THE INVENTION

Imaging of biological tissues and organs assists doctors in both diagnosis and treatment. A variety of medical techniques which are suitable for imaging biological tissues and organs are known. These include traditional x-rays, ultrasound, as well as magnetic resonance imaging (MRI), and computerized tomography (CT). A variety of dyes used in medical imaging have also been described including radio opaque dyes, fluorescent dyes, as well as, colormetric dyes (see e.g., U.S. Pat. Nos. 5,699,798; 5,279,298; 6,351,663; and 6,915,154 and U.S. patent application Ser. Nos. 10/619, 548 and 10/365,028). Imaging techniques and systems using fluorescent dyes have been described for the heart, eye, and other parts of the body (see, U.S. Pat. No. 5,279,298; U.S. patent application Ser. No. 10/619,548, which is incorporated by reference in its entirety). Some dyes can serve both an imaging function, as well as a therapeutic function (see, e.g. U.S. Pat. No. 6,840,933).

SUMMARY

In one embodiment, the invention provides a method of determining the patency of a vessel proximal to a tissue comprising a flap or graft, wound or burn in a subject. The method includes the steps of: (a) administering a fluorescent dye to the subject, (b) applying a sufficient amount of energy to the tissue such that the fluorescent dye fluoresces, (c) obtaining a fluorescent image of the tissue; and (d) observing the image to determine whether one or more vessels proximal to the tissue is patent. The vessel may be in the subdermal plexus. The method may be performed on an animal, and preferably on a human. The fluorescent dye may be a tricarbocyanine dye or an analog thereof. In some cases, it may include a mixture or combination of multiple fluorescent dyes or analogs thereof. The dye may be administered at a concentration ranging from about 2.5 mg/ml to about 25 mg/ml. In some embodiments, it may be administered by injection directly into an artery proximal to the tissue of interest at a concentration of about 0.025 mg/ml. If the tissue of interest is a flap, preferably the adipose side of the flap is imaged. The dye may be administered less than an hour before determining patency. For example, it may be administered more than 30 seconds before determining patency. In some embodiments, the power output of the energy source is modulated.

In another embodiment, the invention provides an imaging system that includes: (a) a computer; (b) an energy source in electrical communication with the computer; (c) a sensor in electrical communication with the computer; and (d) a control whose position is correlated with the amount of electrical current fed to the source.

The control is associated with an electrical circuit which converts the position of the control into an electrical current.

In another embodiment, the invention provides a software product, on computer readable media, for modulating source power. The software product includes program instructions that, when executed, instruct a computer to: (a) capture an image; (b) determine a measure of pixel intensity; (c) compare the measure against a saturation limit; and (d) increase the source power if the measure is less than the saturation limit.

The program instructions may instruct the energy source to increase power only if the power before increase is less than the source power limit. The source power limit is the maximum amount of power that the source can output. The measure of pixel intensity may be substantially any of the following based on one or more images: (a) average pixel intensity of all pixels indicative of fluorescence, (b) peak pixel intensity; or (c) the mean, median or mode of some or all pixels in one or more images. The program instructions may be stored on computer readable media (e.g., a CD, hard drive, etc.), on firmware, or on hardware. The invention further provides a system that includes these program instructions along with (a) a computer; (b) an energy source in electrical communication with the computer; and (c) a sensor in electrical communication with the computer.

In yet another embodiment, the invention provides an imaging system including: (a) a computer, (b) an energy source in electrical communication with the computer, (c) a sensor in electrical communication with the computer, and (d) program instructions, on computer readable media for modulating the source power. Modulation may occur by increasing the source power by about at least 5% to about 10%, such increases may occur every about 0.33 second for example. In another embodiment, the increase may be about 5-10, 10-15, 15-20, or 20-35 watts, such increases occurring periodically, such as about every 0.33 seconds for example. The program instructions may instruct the source to modulate between a starting power level and a maximum power. The starting and maximum power levels of the source may be set in the program instructions and/or may be modifiable by user input.

In another embodiment, the invention provides a method of decreasing the risk of iatrogenesis during a surgical ablation procedure. The method includes the steps of: (a) administering a fluorescent dye to a subject, (b) applying a sufficient amount of energy to heart tissue such that the fluorescent dye fluoresces, and (c) obtaining a fluorescent image of the heart tissue, wherein one or more major vessels are visible in the image. Step (c) may be performed before, during and/or after the surgical ablation procedure. It may be performed on an animal or a human. The dye may be a tricarbocyanine dye or an analog thereof.

BRIEF DESCRIPTION OF THE DRAWINGS

The above and further advantages of the invention may be better understood by referring to the following description in conjunction with the accompanying drawings in which.

DETAILED DESCRIPTION

Figure 1:
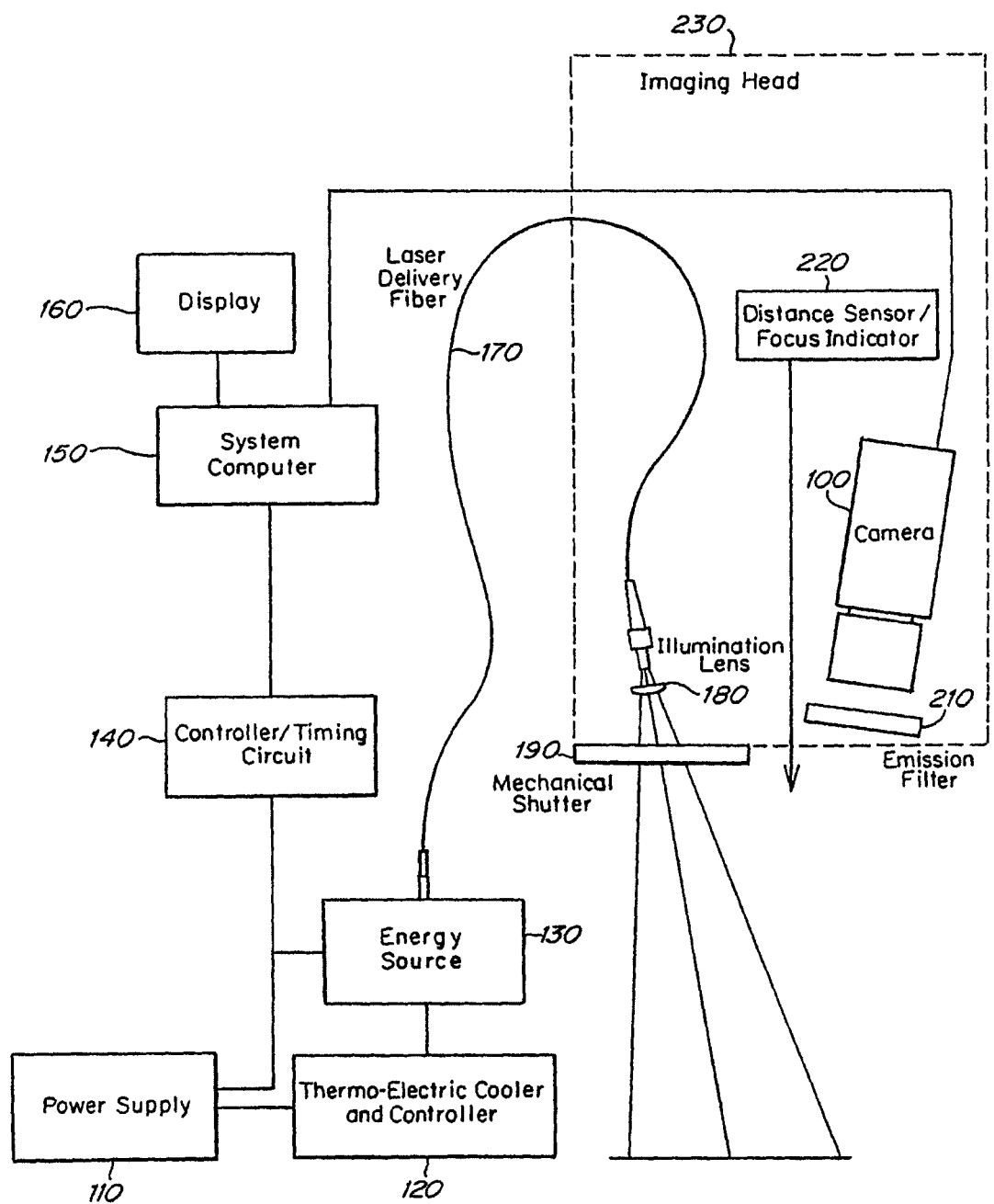
FIG. 1 illustrates an example of an electrical configuration of a system of the invention.

The invention provides methods, program instructions on computer-readable media, and systems for imaging. Certain methods are drawn to imaging damaged tissue, such as flaps, wounds, and burns, flaps, or grafts. Other embodiments are drawn to imaging coronary arteries and veins in the context of certain ablation procedures. The systems and program instructions described herein are applicable to each of these and other imaging applications.

Hereinafter, aspects in accordance with various embodiments of the invention will be described. As used herein, any term in the singular may be interpreted to be in the plural, and alternatively, any term in the plural may be interpreted to be in the singular.

Definitions

As used herein, the term Proximal means within 1 meter, within 500 mm, within 250 mm, within 100 mm, within 10 mm, within 1 mm, or within 0.05 mm of the damaged tissue or skin flap or graft, or within the damaged tissue or skin flap or graft. In some embodiments, the imaged tissue may be a surgically exposed. In other embodiments, the imaged tissue may not be surgically exposed (e.g., a wound visible on the outside of a subject's body, such as a knife stab).

Substantially and About each mean within 10%, preferably within 6%, more preferably within 4% even more preferably within 2%, and most preferably within 0.5%, and even more preferably within the range or number.

Subject as used herein, refers to any animal. The animal may be a mammal. Examples of suitable mammals include, but are not limited to, humans, non-human primates, dogs, cats, sheep, cows, pigs, horses, mice, rats, rabbits, and guinea pigs.

Computer, as used herein, refers to a conventional computer as understood by the skilled artisan. For example, a computer generally includes a central processing unit that may be implemented with a conventional microprocessor, a random access memory (RAM) for temporary storage of information, and a read only memory (ROM) for permanent storage of information. A memory controller is provided for controlling RAM. A bus interconnects the components of the computer system. A bus controller is provided for controlling the bus. An interrupt controller is used for receiving and processing various interrupt signals from the system components. Mass storage may be provided by diskette, CD ROM or hard drive. Data and software may be exchanged with computer system via removable media such as the diskette or CD ROM. A CD ROM drive is connected to the bus by the controller. The hard disk is part of a fixed disk drive that is connected to the bus by a controller. User input to the computer may be provided by a number of devices. For example, a keyboard and mouse may be connected to the bus by a controller. An audio transducer that might act as both a microphone and a speaker may be connected to the bus by an audio controller. It will be obvious to those reasonably skilled in the art that other input devices, such as a pen and/or tablet may be connected to the bus and an appropriate controller and software, as required. A visual display can be generated by a video controller that controls a video display. Preferably, the computer further includes a network interface that allows the system to be interconnected to a local area network (LAN) or a wide area network (WAN). Operation of the computer is generally controlled and coordinated by operating system software, such as the Solaris operating system, commercially available from Sun Microsystems, the UNIX® operating system, commercially available from The Open Group, Cambridge, Mass., the OS/2® operating system, commercially available from International Business Machines Corporation, Boca Raton, Fla., or the Windows NT operating system, commercially available from MicroSoft Corp., Redmond, Wash. The operating system controls allocation of system resources and performs tasks such as processing scheduling, memory management, networking, and I/O services. In particular, an operating system resident in system memory and running on the central processing unit coordinates the operation of the other elements of the computer.

Methods of the Invention

In certain embodiments the invention provides a method of determining the patency of at least one vessel within or proximal to a skin flap or graft, or wounded, burned or otherwise damaged tissue in a subject. Thus, by determining the depth at which the tissue of interest is perfused, the healthcare provider can determine the extent of injury or viability of the graft or flap.

The invention also contemplates, in some embodiments, obtaining a plurality of images. The plurality of images may be compared to each other to determine the effectiveness of a therapy or treatment, e.g. resecting a flap to a body area in need thereof.

In certain embodiments, the method comprises a) administering a fluorescent dye to the subject; b) applying a sufficient amount of energy to the tissue of interest such that the fluorescent dye fluoresces; c) obtaining a fluorescent image of the tissue of interest (e.g., proximal to a damaged tissue, a flap or graft, etc.); and d) observing the image to determine the degree of perfusion in the tissue of interest. As a non-limiting example, the skilled artisan will understand that a fluorescent signal indicates blood flow. As an example, but not as a limitation, a continuous signal from a dye that is uniform in thickness may indicate patency. As another non-limiting example, an image displaying jagged edges, or a change in thickness may indicate stenosis or incomplete perfusion. Similarly a discontinuous signal may indicate occlusion or incomplete perfusion. A lack of a signal may indicate lack of perfusion.

In other embodiments, the invention provides methods for mapping coronary arteries and veins during a surgical ablation procedure and also for preventing unintended injury during such procedures. It is contemplated that certain methods of the invention might be used in a number of surgical ablation procedures used to treat atrial fibrillation. Such procedures may be "minimally invasive" or traditional "open" surgery, and may be combined with other surgical therapies such as bypass surgery, valve repair, or valve replacement. Examples of surgical ablation procedures within the context of the invention include:

(a) The Maze procedure. This is an open-heart surgical procedure. A surgeon makes incisions in the heart to interrupt the conduction of abnormal impulses and to direct normal sinus impulses to travel to the atrioventricular node. Scar tissue is then formed, thus causing electrical impulses to be blocked from traveling through the heart.

(b) Minimally invasive surgical ablation utilizing an endoscope.

(c) The modified Maze procedure. Ablation is carried out using a catheter to deliver energy that creates controlled lesions on the heart. Upon healing, the heart forms scar tissue.

Thus, in one embodiment, the invention provides a method for preventing unintended injury (e.g., iatrogenesis) during a surgical ablation procedure. The method includes the steps of: (a) administering a fluorescent dye to the subject; (b) applying a sufficient amount of energy to heart tissue such that the fluorescent dye fluoresces; and (c) obtaining a fluorescent image of one or more arteries or veins perfusing the heart. The image is viewed to determine the position of major vessels feeding into or from the heart. Images are preferably obtained in real time, and may be obtained before the start of a procedure so that the surgeon can determine where he will ablate the heart such that he is not likely to injure a major blood vessel feeding from or to the heart. The major vessels of the heart include the following and their branches: Right Coronary Artery, Acute Marginal Artery, Posterior Descending Artery, Left Anterior Descending Artery, Diagonal Arteries, Oblique Marginal Artery, Circumflex Artery, and Left Coronary Artery. The major vessels of the heart also include coronary veins and their branches. The surgeon will be able to identify these major arteries and veins based on their placement on the heart as well as that they will generally appear larger than minor vessels such as capillaries because they carry more blood. The surgeon may further obtain images during the ablation procedure to determine the position of one or more surgical instruments, catheters, endoscopes or other surgical devices in relation to major vessels. The surgical instruments, catheters, or endoscopes may be labeled with a marker (e.g., a fluorescent marker) to assist in determining its location. In some embodiments, an image may be obtained after the completion of a surgical ablation procedure in order to confirm that a major vessel has not been severed or otherwise injured by the surgical ablation procedure. As a non-limiting example, a lack of fluorescence in areas that previously fluoresced indicates a loss of perfusions. As another non-limiting example, scattered fluorescence may indicate bleeding or other injury. Thus, the surgeon will be able to confirm that there is no unintentional bleeding at the end of the procedure, and immediately take any required remedial actions if bleeding is present.

In some embodiments, the methods of the invention may further include the step of adjusting the power level of the laser. This may be done as the laser is firing or between multiple laser firings, e.g., between pulses in a pulse train or between pulse trains. In certain embodiment, the device is configured to allow the user to modify the power output of the laser, as described below. Thus, if a user notices that the image is "blooming", i.e., too bleached, he can turn down the power until the image is sufficiently clear. In other embodiments, power may be modified or modifiable one or more times during a medical procedure to view vasculature at multiple depths in the tissue of interest or proximal thereto.

Dyes

Suitable fluorescent dyes include any non-toxic dye which fluoresces when exposed to radiant energy, e.g. light. In certain embodiments the dye is a fluorescent dye that emits light in the infra red spectrum. In certain embodiments the dye is a tricarbocyanine dye such as indocyanine green (ICG). In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The aforementioned dyes may be mixed or combined in certain embodiments. In some embodiments dye analogs may be used. A dye analog includes a dye that has been chemically modified, but still retains its ability to fluoresce when exposed to radiant energy of an appropriate wavelength.

In some embodiments the dye may be administered intra-arterially, intravenously, subcutaneously or orally. Preferably, the dye is administered parenterally. In some embodiments, the dye may be injected into the patient at a location proximal to the skin flap or graft, or damaged tissue of interest. It may be administered as a bolus injection. In some embodiments the bolus injection may comprise a volume of about 0.5 ml. In certain embodiments the bolus injection may comprise a volume in the range of about 0.1 ml to about 10 ml. Where multiple dyes are used they may be administered simultaneously, e.g. in a single bolus, or sequentially, e.g. in separate boluses. In some embodiments the dye may be administered by a catheter, e.g. during a minimally invasive procedure.

The dye may be administered at a suitable concentration such that the fluorescence may be detected when the appropriate wavelength of radiant energy is applied. In some embodiments where the dye is ICG a suitable concentration is about 0.03 mg/ml at the site of detection. In other embodiments a suitable concentration of ICG is in the range of about 0.003 mg/ml to about 75 mg/ml. In some embodiments the ICG is administered in the range of about 1 mg/kg body weight to about 6 mg/kg body weight. In certain other embodiments the dye is administered at a concentration of about 0.5 mg/kg body weight. As another example, the dye is administered in a range of about 0.01 mg/kg body weight to about 3 mg/kg body weight. In certain embodiments a suitable maximum daily dose of ICG may be administered to a subject. The maximum daily dose may be in the range of about 70 mg-about 140 mg.

The dye may be provided as a lyophilized powder or solid. In certain embodiments it may be provided in a vial, e.g. a sterile vial which may permit reconstitution with a sterile syringe. It may be reconstituted using any appropriate carrier or diluent. Examples of carriers and diluents are provided below. In certain embodiments the dye may be reconstituted at a concentration in the range of about 0.001 mg/ml-100 mg/ml. In other embodiments the dye is reconstituted to a concentration of about 10 mg/ml, about 20 mg/ml, about 30 mg/ml, about 40 mg/ml, about 50 mg/ml. The dye may be reconstituted, e.g., with an aqueous solvent immediately before administration. In certain embodiments of the invention, the dye may be administered at a concentration of about 1-10 mg/ml.

In certain embodiments the dye may be administered to the subject less than an hour in advance of obtaining an image. In some embodiments the dye may be administered to the subject less than 30 minutes in advance of obtaining an image. In yet other embodiments the dye may be administered at least 30 seconds in advance of obtaining an image. In still other embodiments the dye is administered contemporaneously with obtaining an image.

Diluents and Carriers

Any diluent or carrier which will maintain the dye in solution may be used. As an example, in certain embodiments where the dye is ICG the dye may be reconstituted with water. In other embodiments where the dye is ICG, the dye may be reconstituted with an alcohol, e.g. ethyl alcohol. In some embodiments once the dye is reconstituted it may be mixed with additional diluents and carriers. In some embodiments the dye may be conjugated to another molecule, e.g., a protein, a peptide, an amino acid, a synthetic polymer, or a sugar e.g., to enhance solubility or to enhance stability.

Additional examples of diluents and carriers which may be used in the invention include glycerin, polyethylene glycol, propylene glycol, polysorbate 80, Tweens, liposomes, amino acids, lecithin, dodecyl sulfate, phospholipids, deoxycholate, soybean oil, vegetable oil, safflower oil, sesame oil, peanut oil, cottonseed oil, sorbitol, acacia, aluminum monostearate, polyoxylethylated fatty acids, and mixtures thereof. Additional buffering agents may optionally be added including Tris, HCl, NaOH, phosphate buffer, HEPES.

Systems of the Invention

In certain embodiments the invention provides a system for imaging, see, e.g., FIG. 1.

System Overview

FIG. 1 illustrates an example of an electrical configuration of a system of the invention. In certain embodiments, power supply 110 provides energy to thermo-electric cooler and controller 120, energy source 130 and controller/timing g circuit 140. The controller 120 controls the temperature of energy source 130. For example, the temperature of a diode laser affects its operating wavelength, (e.g., a 0.3 nm shift per degree Celsius). In some embodiments, as described herein, the energy source 130 may not be a diode laser, and hence a controller 120 may not be necessary. Controller/timing circuit 140 times the energy source 130 to the detector/camera 100 through computer 150. It also includes image processing software on computer 150 readable medium. Computer 150 is in electrical communication with camera 100 and display 160. Display 160 receives image data from computer 150 and displays it. As described above, in some embodiments, the radiation source 130 is a laser. It has a fiber 170 through which light energy is transmitted. Fiber 170 connects to illumination lens 180 through which light is illuminated when mechanical shutter 190 is open. An emission filter 210 may be used to filter light above or below the wavelengths at which the fluorescent dye is excited. In other embodiments, the energy source 130 may be an LED. It would directly illuminate the tissue of interest (i.e., no fiber 170 may be required.) Camera 100 captures radiation emitted by the dye after it is excited and transmits detected data to computer 150. The lens 180, fiber 170, and camera 100 are part of imaging head 230. The head 230 may be an articulating head. In some embodiments, head 230 further includes a distance sensor/focus indicator 220. The components of the systems of the invention are further described herein.

In certain embodiments, the system comprises: a) an energy source 130 capable of emitting sufficient energy such that the fluorescent dye fluoresces; and b) an imaging head 230. The system is configured for use with methods disclosed herein. In some embodiments, the system further includes one or more of: c) an articulating arm; e) a computer 150 and monitor; d) image processing software; e) an electrical power source; and f) a housing for containing some or all of a-f, wherein the housing is portable. In some embodiments the system may also comprise at least one of the following: a motion sensor; a distance sensor 220; a sterile drape; and a printer. The system will preferably include an instruction booklet. The system may be portable and thus may be transported in and out of the operating room. The system may be self standing and thus does not require to be held by a physician or a technician. In other embodiments, the system may be configured to have an imaging head that a physician may hold.

In certain embodiments of the invention radiant energy is applied to the tissue of interest, in an amount sufficient to cause a fluorescent dye to fluoresce thereby permitting the tissue of interest to be imaged. In some embodiments the source of the energy is a laser. The laser may be comprised of a driver and diode. Preferably, the laser is a high power laser diode (HPLDs). Examples of HPLDs include AlInGaAsP lasers and GaAs lasers which are well known in the art. Such sources can be single diodes (single emitters), or diode-laser bars, which are made from edge emitting semiconductor chips. The laser may optionally include a filter, e.g. a bandpass filter, to ensure that the emitted radiation is of a substantially uniform wavelength. The laser may comprise optics for diverging the laser. The optics may be adjustable permitting variation in the field of illumination. The adjustable optics may also be used to provide even illumination over a given area.

In some embodiments the source output is continuous or quasi continuous. In other embodiments the laser output is pulsed. The pulsed output may be synchronized with image acquisition by using a pulse generator. In some embodiments the laser pulse may last for at least 3 femtoseconds. In some embodiments the laser output lasts for about 30 seconds. In other embodiments the laser output lasts about 0.5 seconds-about 60 seconds. A suitable repetition rate for the pulsed laser may be in the range of any of the following: about 1 Hz-about 80 MHz, about 10 Hz-about 100 Hz, about 100 Hz-about 1 kHz, about 1 kHz-about 100 kHz, about 100 kHz-about 80 MHz. In some embodiments the laser may be operated at power output of about 1.8, about 2.2, or about 2.5 watts. In other embodiments the laser may be operated at power output in the range of about 1-about 4 watts. In still other embodiments the average power is less than 5 watts.

In some embodiments the source of the energy is an incandescent light with an appropriate filter so as to provide a suitable wavelength of light to induce the fluorescent dye to fluoresce. In yet other embodiments the light source is a light emitting diode (LED).

In some embodiments the energy may have a wavelength in the range of 150 nm-1500 nm. The energy may be comprised of infra red light. In some embodiments the administered light has a wavelength of about 805 nm. In certain embodiments the administered light has a wavelength in the range of about 805 nm-850 nm. The light energy may be administered at a wavelength which is shorter than the collection wavelength, i.e. detection wavelength. The light energy may be administered diffusely so as not to damage the irradiated tissue. In some embodiments the light is administered over an area of about 7.5 cm×7.5 cm. In other embodiments the light is administered over an area in the range of about 1 cm×1 cm to about 20 cm×20 cm. Preferably, the area is about 25-100 cm$^2$. As described above, multiple dyes may be used in some embodiments. In these embodiments, multiple light sources may be used, e.g., a first laser to excite a first dye and a second laser to excite the second dye. The skilled artisan will understand that the light source will be chosen or configured to excite a particular dye. In other embodiments, a single light source may be configured to excite multiple dyes, e.g., by alternating the wavelength at which energy is emitted.

The imaging head 230 may be comprised of a light sensor, e.g., a camera 100. Image acquisition may be achieved using any sensor capable of detecting a fluorescent signal. Examples include silicon based sensors, composite metal oxide semi oxide (CMOS) sensors and photographic film. In one embodiment the sensor comprises a camera, e.g. charge coupled device (CCD). Examples of a CCD include the Hitachi KP-M2; KP-M3 (Hitachi, Tokyo, Japan).

The camera may be comprised of a means for focusing the image. In certain embodiments the invention contemplates a manual means for focusing an image. In other embodiments the invention contemplates an automated means for focusing an image. The camera may further be comprised of a lens system that permits magnification of an image field.

In some embodiments, the relative positioning of the camera and laser is fixed so as to enhance clarity and minimize background noise. In these embodiments, the laser is located at an angle of less than about 85° with respect to the axes of the laser and the camera. In other embodiments, the laser is located at an angle from about 20° to about 70° with respect to the axes of the laser and the camera. In some embodiments, the laser is located at an angle greater than about 85° with respect to the axes of the laser and the camera. Such an angle may be, for example, 90°.

In certain embodiments the camera relays the captured image to an analog to digital converter and then through image capture and processing software running on a computer. The digital image of the fluorescing agent, corresponding to the tissue of interest or blood vessels therein, may then be displayed on a monitor and recorded by the computer or a peripheral device. The image may be stored in any suitable medium, e.g., a hard drive, an optical disk, magnetic tape. The camera may also direct images to a television/VCR system such that the images may be displayed in real time, recorded and played back at a later time.

The imaging head 230, may in some embodiments also contain the energy source 130, e.g. the laser. In some embodiments the laser contained within the imaging head 230 provides a nominal ocular hazard distance (NOHD) of about 27 cm. The NOHD is the distance at which the beam irradiance or radiant exposure equals the maximum permissible exposure. In certain embodiments the imaging head 230 is joined to the housing by virtue of the articulating arm.

In some embodiments, the articulated arm provides six degrees of freedom for the imaging head 230. The imaging head 230 can be translated and positioned in three linear movements (X, Y and Z), and three angular movements (pitch, yaw and roll). Pitch is the rotation of the imaging head 230 about the Y axis. Roll is the rotation of the imaging head about the X axis and Yaw is the rotation of the imaging head about the Z axis.

The articulated arm is comprised of three sections, the horizontal section, the articulated section and the yoke. The horizontal section attaches to the cart, or housing, and provides movement along the horizontal axis (X axis and also roll) and can move in 270 degrees of freedom. The articulated section is hinged in the middle of its length forming two segments. Each segment can rotate with 90 degrees of freedom in one axis. The articulated section provides movement in the vertical axis (Z and also X and Y). The yoke section is a curved section that attaches to the distal end of the articulated section. The yoke has two rotational attachment points. One point attaches to the articulated arm and the other to the imaging head 230. The yoke provides the imaging head 230 two rotational degrees of freedom (pitch and yaw). The articulating arm thus provides a means for positioning the imaging head 230 directly over the subject. The yoke is analogous to the wrist 310 and the horizontal section is analogous to the arm 300 in FIG. 4.

In certain embodiments the imaging head 230 is positioned above the patient and the appropriate field of view is obtained with the aid of real time images on a computer 150 monitor. The physician or other user may adjust the range of focus, e.g., by intermittently observing images on the computer 150 monitor. In another embodiment two laser pointers are provided, e.g., one at each end of the imaging head 230. The laser beams may radiate green light, red light, or any other wavelength of light. Preferably, the wavelength is in the visible spectrum so that specialized detectors (aside from the human eye) are not required to view the beams. The laser beams from the pointers point down toward the patient and provide a means of focusing the camera 100, without the need to look away from the patient, e.g., at a computer 150 screen 160. Preferably, two or three lasers are used. The lasers are configured so that then the two dots from the laser beams converge at the centre of the image, thus allowing easy determination of the location of the center. The device may be provided with buttons that allow for manually turning the laser pointers on and off. The buttons may be covered by a sterile drape, but may protrude enough to facilitate ease in switching the laser pointers on and off.

In certain embodiments the computer 150 is a personal computer comprising at least 512 Megabytes of random access memory (RAM) and at least 10 Gigabytes of storage. In some embodiments the computer 150 may contain a Pentium IV processor (Intel, Santa Clara, Calif.). In some embodiments the computer 150 may also have a CD and DVD drive. The drive may have read and write functionality. The system also provides image processing software.

In certain embodiments an endoscope may be used to excite a fluorescent dye and detect its fluorescence, e.g., for interventional applications. It includes a sensor and a source of radiant energy. The endoscope may be comprised of optical fibers. In certain other embodiments a microscope comprising a sensor and radiation source may be used, e.g., a surgical microscope. In some embodiments the sensor comprises a video camera. In certain embodiments the sensor may capture images at the rate of at least 10 per second, at least 15 per second, at least 20 per second, at least 30 per second, or at least 50 per second. Thus in certain embodiments the invention contemplates a plurality of images. In other embodiments the invention contemplates one image.

Figure 2:
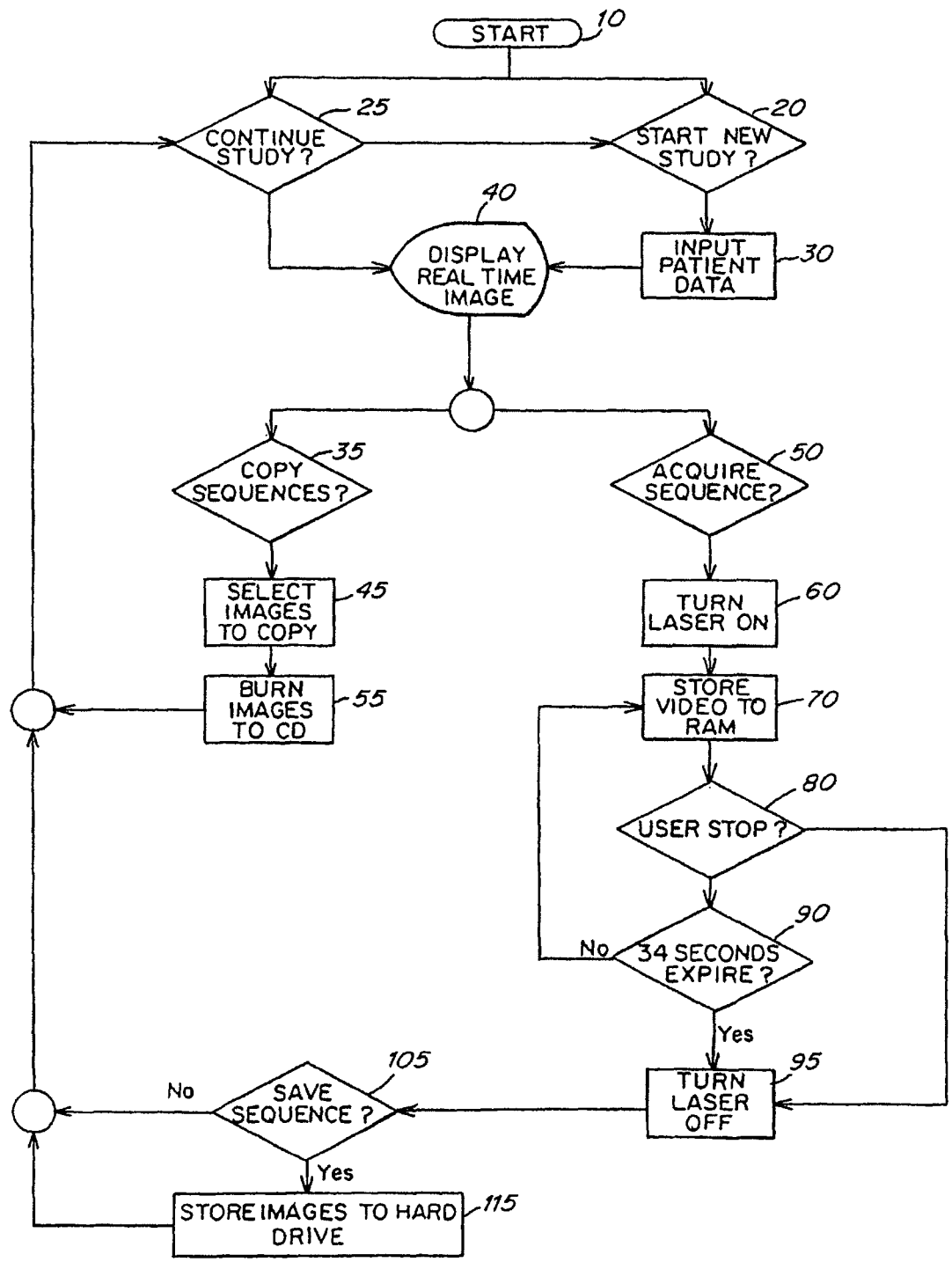
FIG. 2 illustrates a method of the invention.

FIG. 2 illustrates a method of the invention. This method may be carried out by program instructions stores on computer readable media, hardware or firmware. The skilled artisan will understand that such software includes instructions stored on computer-readable medium. When executed, the software program provides instructions to the computer processor as described below. The skilled artisan will further understand that the computer is in communication with the laser, sensor and display as described herein.

At start (step 10) the user may be presented with multiple dialog boxes or other common user interface paradigms. For example, the user may be queried about whether he wishes to start a new study (step 20). If the user indicates that he does, he may be instructed to input or otherwise select a patient for the study. For example, the user may be prompted to choose a name from a list linked to a database that is accessible to the computer. Alternately, he may be prompted to input a patient identifier. The computer may then access the database to determine the existence of additional information associated with the patient, and preferably to obtain such information. In a preferred embodiment, the software requires the user to input or otherwise select values for Patient First Name, Last Name and ID number fields. Most preferably, sufficient information is inputted or otherwise loaded so that images may be stored according to the Digital Imaging and Communications in Medicine (DICOM) standard. The DICOM Standard is a product of the DICOM Standards Committee and its many international working groups. Day-to-day operations are managed by the National Electrical Manufacturers Association (Rosslyn, Va.). The standard is publicly available at the website http://medical-.nema.org/, and is incorporated herein by reference in its entirety.

After patient data is inputted, the monitor or other display displays images captured by the camera or other sensor in communication with the computer (step 40). At this point, the user can change the position, orientation, gain or other parameter of the camera to obtain a desired view of the patient.

Alternately, the user may choose to continue a study (step 25) at start 10. Upon such indication, the process proceeds to step 40.

Once the image is displayed, the user is prompted to indicate whether he wishes to copy sequences (step 35) or acquire sequence (step 50). The term "sequences" refers to data associated with real-time images captured by a camera or other sensor in communication with the computer. Once the user indicates that he wants to acquire images from the sensor in step 50, the computer causes the laser to turn on, and it stores the video sequence obtained from the sensor in RAM (step 70). Real time images continue to be displayed on the display. The user is then queried about whether he wishes to turn the laser off (step 80). If he indicates that he does, the computer causes the laser to shut off (step 100). Alternately, if the user does not indicate that he wants to shut off the laser, the computer determines whether a pre-determined amount of time (e.g., 34 seconds) has elapsed from step 60. Once that pre-determined amount of time has elapsed, the computer causes the laser to shut off. The video sequences continue to be stored in RAM until the laser is turned off. Once the laser is turned off, the user is queried as to whether he wishes to save the sequence (step 105). If he indicates in the affirmative, then the sequences are stored to hard drive (step 115) or other media.

Returning now to step 40 for purposes of describing the software, once the real time image is displayed, the user is queried as to whether he wishes to copy sequences (step 35). If the user indicates that he does, the images associated with the study are selected and burned on compact disk or other selected media (step 55). Alternately, the software may allow the user to select specific images for storage on selected media. Preferably, the image(s) are stored in a format that is compatible with a picture archiving and computer system, for example in a DICOM format.

In another embodiment, the camera may also direct images to a LCD monitor or other display (e.g., television/VCR system, etc.) such that the image(s) may be displayed in real time and/or recorded and played back at a later time. Since the image(s) may be used to guide all or part of the surgical procedure, the image(s) may be displayed through out the length of the surgical procedure. In other embodiments, the image(s) may be displayed for less than the entire length of the surgical procedure. In another embodiment the software permits manipulating the images after acquisition, such as zooming, region of interest selection, change of brightness and contrast, and displaying multiple images simultaneously.

In certain embodiments the image processing software permits selection of the optimal image for analysis. In some embodiments the image processing software may permit manipulation of contrast. In some embodiments the image processing software can permit manipulation of resolution. In another embodiment the image processing software can permit manipulation of the number of pixels in a field. In another embodiment the image processing software may permit control of the rate at which images are acquired. The software may be able to determine the relative contrast of one image with another, and thus select the images having the greatest contrast for analysis, e.g., images of transplanted organs emitting detectable fluorescence.

In certain embodiments software on computer readable media may be used to compare images of pre and post treatment vessels to determine flow within the vessel, e.g., blood flow, or used to compare pre and post tissues to determine change in tissue perfusion. A change in fluid flow through one or more vessels would be determined where the first and second images are fluorescent images of vessels, e.g., blood vessels. A change in tissue perfusion would be determined where the first and second images are fluorescent images of tissue. In certain embodiments, the software includes an algorithm, e.g., pixel detection algorithm. In certain embodiments, the software includes instructions for determining the pixel intensities or brightness of two registered images, e.g., by a pixel detection algorithm, and further includes instructions for determining the change in pixel intensities between the two images. For example, a difference may be determined by subtracting the intensity of a first pixel in the first image from a second pixel in the second image. In some embodiments, the difference between an individual, mean, median or mode of some or all pixels in a first image and the individual, mean, median or mode, respectively, of some or all pixels in a second image may be determined. In some embodiments, the two images are registered and correspond to the same or approximately same space or portion of the body part being imaged.

An increase in intensity in pixels pre to post treatment indicates greater perfusion in tissue or fluid flow through vessels, while a decrease may indicate a decrease in perfusion in tissue or flow through vessels. In another embodiment, the software includes instructions for determining the number of pixels in two or more images that are indicative of fluorescence and determining the difference between these determined numbers. In some embodiments, the difference is determined as a function over time. An increase in the number of pixels indicative of fluorescence is indicative of an increase or greater patency or flow, while a decrease suggests less patency or flow.

In some embodiments, the two or more images are registered. For example, a solid state accelerometer is used to determine position of the imaging head with respect to normal (earth's gravity). The accelerometer measures acceleration typically in units of meters/second squared. The steady state signal or DC value of this signal can be used to determine inclination with respect to vertical. The derivative with respect to time of the accelerometer signal may be used to determine velocity of the imaging head. The skilled artisan is familiar with other registering techniques.

Figure 4:
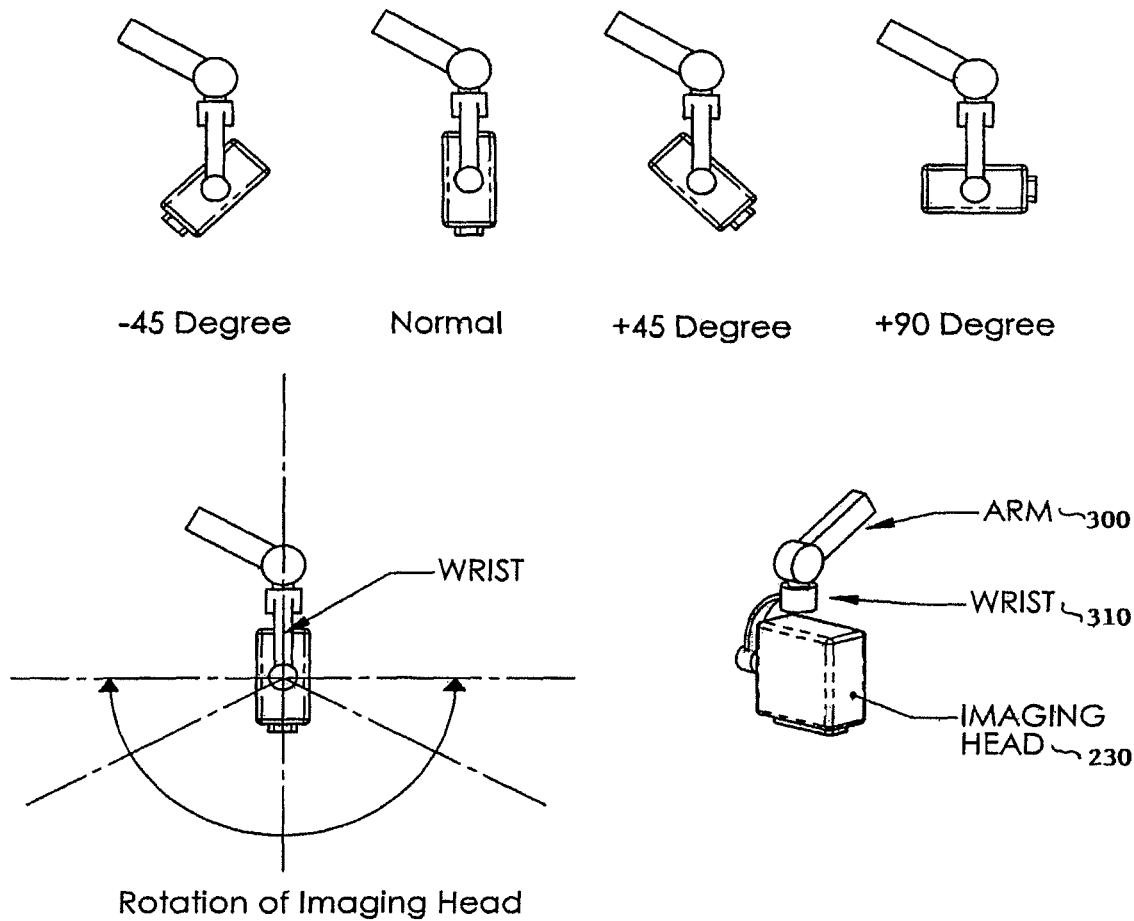
FIG. 4 illustrates certain embodiments of a system of the invention.

In some embodiments the images are registered by making sure that the sensors and the power source remain at substantially the same angles in relation to each other and to normal when taking two or more images. For example, FIG. 4 illustrates an exemplary imaging arm 300 which connects to an imaging head 230 through a wrist 310. The arm is mechanically connected to a cart or housing. A potentiometer is used to measure the angle of the imaging head 230 against normal. The potentiometer is mounted to a wrist 310 of the imaging arm 300. The potentiometer shaft is connected to a point on the imaging head that rotates around the wrist 310. As the head 230 is rotated, the shaft of the potentiometer is forced to rotate in direct proportion to the angle of the head 230. The angle is essentially the angle formed between the wrist 310 and head 230. Thus, preferably, the wrist 310 is always oriented to Normal (Vertical, or Plumb with respect to gravity). The signal from the potentiometer is measured via the electronics/computer of the system 150.

The invention further provides imaging systems that allow the user to modulate the power of the energy source, e.g., laser. The system may be any imaging device, including endoscopes, that include an energy source for exciting a dye and a sensor for sensing energy emitted by the excited dye. The system displays an image based on the energy sensed by the sensor. Preferably, the dye is ICG. For example, suitable systems include endoscopes and systems, such as those disclosed herein, as well as the systems disclosed in U.S. Pat. Nos. 6,944,493, 6,915,154, 6,443,976, 6,351,663, U.S. application Ser. Nos. 10/477,237, 10/619,548, and 11/114,501, as well as PCT applications such as PCT/US06/016957 and PCT/US06/016101, each of which is hereby incorporated by reference in its entirety. The system may include a knob, a slide switch or other control that is in electrical communication with the energy source, and is associated with electronic circuits which convert the user's control position into an electrical current. Thus the electrical current fed to the source is modified by movement of the control. In some embodiments, the amount of electric current is in direct proportion to the position of the user's control. The control may allow the output power to be adjusted from 0 Watts to the maximum power of the source.

Figure 3:
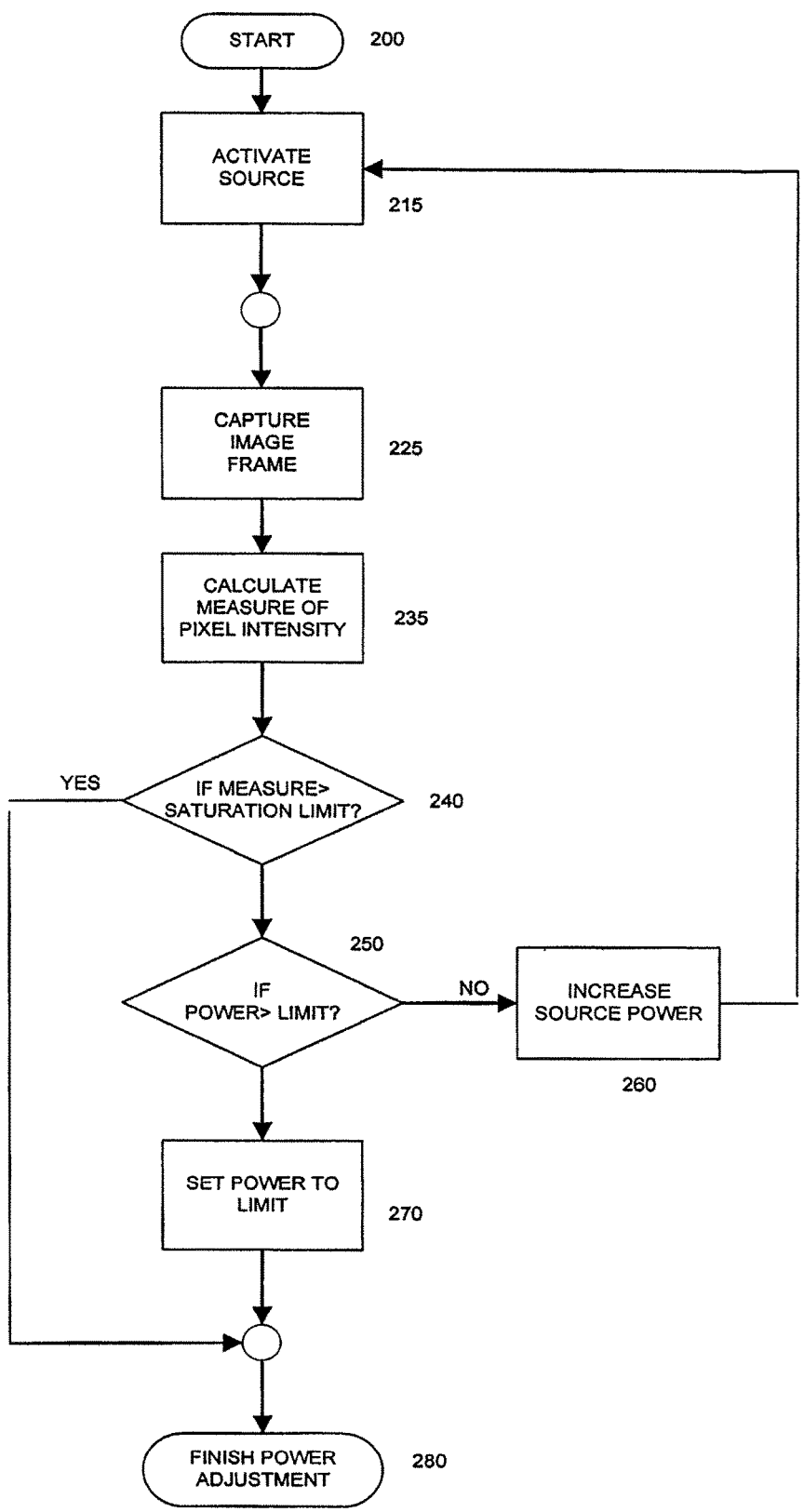
FIG. 3 illustrates another method of the invention.

The invention further provides systems having program instructions for automatically modulating the power output of the energy source. These systems may be any imaging systems that include a power source for exciting a dye, a sensor for sensing the emitted radiation from the dye and a computer, such as the systems described herein including endoscopes. The instructions may be on computer readable media, such as media associated with the computer or on firmware or hardware. Referring now to FIG. 3, after start (step 200) the laser or other source is activated (step 210). Preferably, the source is powered at a relatively low level. For example, if the source is a laser, it might be electronically instructed to first fire at a relatively low power (e.g., less than 5%, 10%, 15%, 20%, 25%, 30%, 35%, 40%, 45% or 50% of maximum source power). An image is captured (step 225) and a measure of pixel intensity is determined (step 235). In step 240, it is determined whether the determined measure of pixel intensity is greater or lower than a saturation limit intensity. If the determined measure of pixel intensity is indicative of non-saturation and the power of the system is below the source power limit or the system power limit (step 250), power is increased in step 260. It is preferably increased relatively slightly. For example, the source power level might be increased by less than about 5%, less than about 10%, less than about 15%, less than about 20%, or less than about 25% at step 260. Preferably, the increase is between about 2 and about 5%, and most preferably between about 2 and about 10%. The source either fires again (e.g., a pulse part of a pulse train) or continues to fire (e.g., a continuous wave source) in step 210 and an image is again captured (step 220). Referring again to step 240, if it is determined that the determined pixel intensity is suggestive of saturation, no further adjustments are made (step 280). Thus, the system will preferably continue to acquire images and/or excite fluorescent dye (step 280).

The "saturation limit" (used in step 240) may be encoded into the program instructions. In other embodiments, the saturation limit may be adjustable by a user, for example through a graphic user interface. An example of a saturation limit might be an intensity of 200 out of a maximum of 255. This would be for an 8-bit depth image so the brightness of the image ranges from 0 to 255. Thus, the saturation limit is at least about 60%, about 70%, about 78%, about 82%, or about 85% of the maximum intensity value based on the image depth (e.g., 8-bit, 16-bit, 32-bit, etc.)

There are several measures of pixel intensity that can be used to determine whether the pixel intensity is suggestive of saturation. For example, the peak intensity level of one or more images may be compared against the saturation limit. Alternately, the mean intensity level of all pixels may be compared against the saturation limit. In other embodiments, the mean intensity level of all pixels that have an intensity indicative of fluorescence may be compared against the saturation limit. In yet other embodiments, the mode or median value of all pixels having an intensity indicative of fluorescence may be compared against the saturation limit.

Another way to determine whether image pixel intensity is greater than the saturation limit would be to calculate the total photonic emission of the amount of dye administered. Thus if an intravenous injection of dye is made, with a known volume of dye at a known concentration, then we can calculate the area of the resulting brightness and compare it to the theoretical amount of brightness that could be observed.

For example, image size is determined from the optical magnification. This magnification is a mapping of the camera's detector cells (pixels) into the object space. For example, a CCD camera may be used having a detector with pixel dimensions of 6.5 μm×6.5 μm. The lens used with the camera may have a 25 mm fixed focal length lens. The field of view (FOV) with this camera is 19.5° in height. The nominal operational distance of the object being viewed may be 304.8 mm (12.0"). The horizontal length in the Field of View (FOV) at 304.8 mm will be approximately 104 mm. The number of horizontal pixels is 696. Thus the 104 mm is divided equally among these pixels. The resulting ratio is 149.4 μm/pixel. Thus, for example, the system may determine the number of pixels representative of fluorescence and multiply this number of pixels by 149.4 μm/pixel to determine the size of fluorescing area.

The optimal situation for determining flow is to detect the edge separating the fluorescing blood and the non fluorescing blood. This transitional edge will travel down a vessel at the rate of the blood flow. The software can detect the front edge, between dark and bright, also called the "wave front" and measure the distance over which this front travels and also the time it takes to travel this distance. From these two values one can calculate velocity. Flow is then derived from a calculation of the cross sectional area of the vessel (i.e., by determining the real life area represented by each pixel to thus determine the radius or diameter of the vessel).

As a non-limiting example, a preferred system power limit is 1.80 W. This limit may be effected by changes to the system, e.g., addition of cameras.

In some embodiment, the system includes other program instructions for automatically modulating the power of the source 130. For example, the system may continuously modulate power from about 0% of the source 130 power limit or system power limit to the power associated with the saturation limit or source power limit. As another non-limiting example, the instructions may cause the power of the source 130 to increase incrementally by about 5 to about 10% every e.g., about 0.33 seconds and/or every $10^{th}$ frame (starting from about 5% of source 130 power limit). When the power reaches either the source 130 power limit or the power level associated with the saturation limit, no further modulations may be made. In another embodiment, power can be modulated repeatedly during a surgical procedure. In certain embodiments, the starting power and the maximum power levels may be input by a user (e.g., through a graphic user interface) and/or set in the program instructions.

The system also provides, in certain embodiments, a housing to contain the computer, the monitor, the electrical supply, the printer, and the imaging head. The housing may be portable to permit movement within the operating room or alternatively to permit movement of the system in and out of the operating room. In some embodiments the housing is comprised of at least two wheels. In other embodiments the housing is comprised of four wheels. The wheels may have locks to prevent unwanted movement.

In certain embodiments the housing has a width of about 30 inches, a depth of about 35 inches and height of about 82 inches. In certain embodiments the housing width is less than 45 inches. In certain embodiments the depth is less than 45 inches. In certain embodiments the height is less than 102 inches. The housing is not hand held, and thus the system is not required to be hand held.

The electrical power supply may be comprised of a lock in some embodiments. The lock serves as a safety device to prevent inadvertent activation of the system, in particular activation of the laser.

In some embodiments the system may be comprised of a motion detector. The motion detector determines if the imaging head moves. In certain embodiments the system comprises a distance sensor. The distance sensor determines the distance between the imaging head and another object, e.g. the subject. In some embodiments it incorporates a visual display which provides feedback to a physician so that the laser and camera may be located at a distance from the tissue of interest that is optimal for capturing high quality images, thereby minimizing the need for focusing the camera during the procedure. The motion sensor and distance sensor may each be located on the imaging head, for example.

In some embodiments the system comprises a sterile drape. The sterile drape covers the articulating arm to prevent or minimize the risk of contamination of the subject. The sterile drape may have an aperture in it. The aperture may be covered with a material which is capable of transmitting radiant energy, e.g., infra red light generated by a laser.

Apparatus

Certain embodiments of the invention provide an apparatus which may be used for intra-operative imaging, e.g., in a surgical suite. The apparatus may be portable so that it may be conveniently transported into and out of an operating room. The apparatus may be free standing and thus not require a physician, nurse or technician to hold it. The apparatus may include one or more systems of the invention. In some embodiments the apparatus may also comprise at least one of the following: a motion sensor; a distance sensor; a sterile drape; and a printer. In some embodiments the housing is comprised of at least two wheels. In other embodiments the housing is comprised of four wheels. The wheels may have locks to prevent unwanted movement. The apparatus may also comprise a focusing device, e.g., at least one focusing laser, e.g. a first and a second laser pointer, the first laser pointer positioned at a first end of the imaging head, and a second laser pointer positioned at a second end of the imaging head. The two laser pointers may be provide radiant light in the green wavelength range and may provide a means of focusing the camera.

The apparatus may be of a suitable size so that it is free standing, but is small enough so as not to provide a significant obstruction in an operating room. In certain embodiments the apparatus has a width of about 30 inches, a depth of about 35 inches and height of about 82 inches. In certain embodiments the apparatus width is less than 45 inches. In certain embodiments the apparatus depth is less than 45 inches. In certain embodiments the apparatus height is less than 102 inches.

The invention will now be described in greater detail by reference to the following non-limiting examples.

Example 1

This example illustrates a system of the invention. The imaging devices is made primarily of two subsystems that are primarily optical in nature, an illumination subsystem and a detection subsystem. Other subsystems are primarily electrical or mechanical in nature. The illumination subsystem includes a fiber-coupled, infrared laser, a light guide, and a projector lens. The detection subsystem includes a high-quality imaging lens, a narrow bandpass filter, and a CCD camera. The remainder of the system includes a laser, video display, computer and other auxiliary control circuits. The system is designed with an articulated arm with an imaging head. The imaging head contains the imaging and illumination optics and electronics. The articulated arm allows the illumination and imaging systems to be positioned over the field of operation.

Mounted inside this imaging head are the filter and CCD camera, a distance sensor and the light guide and projection lens. A power delivery optical fiber is routed through the articulated arm connecting the laser to the light guide in a low-loss manner.

Illumination Subsystem

A fiber-coupled diode laser with a nominal 2 W output is used as a light source. Wavelength is specified to be 806 nm, which can be reached through use of a thermo-electric cooler attached to the laser mechanical package. For the nominally 30% efficient laser, a heat load of about 7 W would be offered to the surrounding mechanical structure. The temperature of a diode laser affects its operating wavelength, typically 0.3 nm shift per degree C. Additionally, diode lasers have a maximum operating temperature that must never be exceeded. These factors make a temperature control circuit not merely good engineering practice, but also an environmental requirement to achieve long lifetimes (10,000+ hours).

Since modern diode laser manufacturing practice cannot tightly control the power vs. current characteristic, each diode is different, and the maximum power for each unit will be different. The assembly and calibration procedure will individually set the operating current for each unit differently. Since a requirement of the system is to deliver a fixed amount of power to the patient (2.0 W nominal), the illumination subsystem will be designed with a high enough efficiency to guarantee an excess of power delivered when the laser is run at maximum current. During final calibration of the system, the laser diode current will be decreased from maximum to reach the 2.0 W requirements.

The output spectrum of most diode lasers is not "line-like" as in an ideal laser. The spectrum extends over several nm and usually shows prominent peaks. There is also a broad (several 10's of nm wide) low-level pedestal of power. For most fluorescence excitation applications, the broad spectral output of these high-power laser diodes requires an external excitation filter to prevent overlapping of the laser light with the emission band. Prototype experiments performed have shown that this extra filter is not required to achieve a good signal-to-noise ratio in the detected fluorescent image.

Power Delivery Fiber

The system uses a fiber optic cable to carry to the optical power from the laser diode to the optics. The laser's fiber is a multimode fiber, whose core can support many modes of laser transmission. This transfers power without burning the fiber. The core diameter (which sets the effective emitting area) is about 200 microns. The spatial pattern of light emitting from the fiber end is approximately a top hat (with rounded corners) in angle. The output is characterized by the fiber Numerical Aperture (NA) which is the sine of the half angle corresponding to the HWHM. A typical power delivery fiber would have an output NA=0.15, corresponding to a FWHM of about 17°.

Light Guide

To project a square illumination pattern of roughly 76×76 mm the light from the fiber is coupled to a light guide with a square cross section. The light guide may be made of any number of acceptable glasses (e.g. BK7). Note that some optical glasses (e.g. Pyrex) or clear plastics (e.g. polycarbonate) have a large bubble density or high refractive index in-homogeneity. This can lead to significant extraneous losses. The approximate dimensions are 0.25×0.25×4.00 inches. All faces should be polished to about 50/80 scratch/dig and flat to within about 5 waves. Protective chamfers (usually a good idea) are to be avoided here since they also can lead to significant extraneous losses.

The purpose of the light guide is to homogenize the laser light. The coupling from the fiber is simply an air gap of a few millimeters. The only requirement is that the end-face of the light guide capture all of the emitted cone of light from the fiber. Thus, for 0.22 NA fiber, the fiber is positioned no further away than 14 mm.

The operation of the light guide is now described. At each point on the exit face, the total laser field is the sum of several fields, some of which have undergone one or more total internal reflections. If scattering losses are kept low, the total power reaching the exit face equals the input power from the fiber, minus Fresnel losses at the end-faces. The radiant distribution is no longer a cone emitted from a small fiber core, but a homogenized, square emitter, with maximum angle equal to the fiber cone angle. Homogeneity improves with length of the light guide. Non-sequential ray-tracing calculations show uniformity with about 20% falloff at the edges after only 4 inches of guide. This is not a diffuse emitter, since for each point on the end-face there are certain definite angles of emission.

Mechanical Interface

The light guide has only a mechanical interface. Preferably, the light guide entry face needs to be within 14 mm of the power delivery fiber exit ferrule. If the cone of light is tight enough, the groove can have a depth of 1 mm without significantly attenuating the light.

The entry face is furthermore tilted with respect to the long axis of the light guide. This allows mechanical access to the Fresnel-reflected beam. A photodiode is placed within this "stray" beam as a power monitoring device. A tilt angle of 20° is arbitrarily chosen as a compromise. The larger the angle, the easier it is for photodiode access and space for fiber connector. The smaller the angle, the easier to manufacture without edge chips and the more robust the overall unit. Optically, coatings can minimize the reflection for just about any angle, but for steep angles of incidence, there can be a great difference in the reflection coefficients for the two orthogonal polarizations. It's best to keep the difference small and use near-normal incidence angles.

Projection Lens

To project the object of square-faced emitter to the region of interest about 30 cm away, a simple two-element air-spaced condenser lens is used. Since we want to create an illuminated region of 76.2×76.2 mm from a 6.35×6.35 mm emitter, we need a magnification of 12.0×. This defines the ratio of image to object distance. For 320 mm (allowing some mechanical clearance for packaging), the required object distance is 26.7 mm. This corresponds to using a lens with a focal length of about 25 mm. The positional tolerance here is about ±0.5 mm.

Power Monitor

A photodiode and preamp circuit is included in the illumination subsystem to monitor the power being transmitted to the patient. The photodiode will be observing a small amount of light reflecting from the input face of the light guide. Without an anti-reflective coating, we expect about 4% of the total to be reflected, the usual Fresnel reflection, valid for small angles. To accommodate the reflected light, either the input face will be tilted slightly with respect to the axis of the light guide, or the fiber output will couple to the input face at a shallow angle.

The Fresnel reflections at both exit and entry faces can be either measured or calculated. The transmission of the condenser lens can be either measured or calculated. These characteristics that affect the total power delivered to the patient are quantities which do not change in time. It is a simple matter to generate a linear equation of power delivered to patient versus monitor photocurrent.

Detection Subsystem/Emission Filter

The infrared light from the laser at 806 nm excites fluorescence indocyanine green, which has been injected into the subject's bloodstream. The dye emits fluorescence at a peak wavelength of 830 nm. An emission filter is used to block the scattered laser light and pass the fluorescent light. Hence the filter is a bandpass filter.

The bandpass filter characteristics are a pass band centered at 830±5 nm and a 10 nm FWHM. It has a minimum attenuation in the stop band of OD 4.

[99] The filter blocks the excitation laser light and the ambient light too. Hence, the device may be used in a brightly illuminated operating room.

Imaging Lens

The imaging lens is a commercial quality photographic lens with a male C-mount thread for attachment to the flange on the camera. The speed should be as fast as possible to collect the fluorescent light with the greatest efficiency. An initial specification is one which is commonly available in a variety of focal lengths—f/1.4. The CCD camera contains a CCD image sensor which is 6.45×4.84 mm (½ inch format). With a 16 mm focal length lens (commonly available focal length), the sensor "sees" a field of 122×92 mm, just over the required 75×75 mm.

CCD Camera

The CCD camera used is a commercially available unit from Hitachi. The KP-M2R has a spectral response that peaks at 640 nm and is useful in the NIR. Electrical power requirement is 12 VDC at 180 mA. Video output is via RS-170 on a standard BNC mount.

Specification of Laser Class

To determine the laser class, use 21 CFR 1040.10 as the governing document. We start with a nominal 3 W laser output from the square 6.35×6.35 mm emitter. This radiation is inaccessible during normal operation. It passes through a projection lens to be focused to an image about 300 mm away. It is accessible during normal operation immediately after this lens.

The power through an aperture needs to be known to determine laser class. This will be accomplished by estimating the radiance of the final emitting surface (outer projection lens surface) and calculating the radiant transfer integral. The final surface of the light guide, while not truly diffuse, nonetheless approximates a uniformly emitting area; i.e. the power per small unit area is constant over the area of the emitter. Additionally, the emission is bounded in angle space; very little light is emitted at an angle greater than 8.6° (corresponding to the input fiber NA of 0.15).

A good approximation to the radiance (power per unit area per steradian) can be calculated this way. The total power from the fiber endface is 3 W. There will be approximately the same amount at the final condenser lens surface, assuming the use of good AR coatings on all surfaces. The area covered by the light on the final condenser surface is a square of about 13 mm on a side. Since the spacing from the light guide endface to the final condenser surface is 33.6 mm, simple geometry would give 16.5 mm using the 8.6° emission angle. The refraction at the first lens in the condenser makes this a bit smaller. A ZEMAX™ ray-trace calculation which includes the full refractive effects of all lens surfaces yields 13 mm. The emitting area is 1.69 cm². Since this lens projects an image 75×75 mm at 300 mm away, the new maximum emission angle is 5.9°, corresponding to a new solid angle of 33.3×10⁻³ sr. Dividing the power by the area and the solid angle gives L=53.3 W/cm² sr.

The radiant transfer of power t from a source (subscript s) to a detector (subscript d) is $$\Phi = \int\int \frac{L\cos\theta_s \cos\theta_d}{s_{sd}^2} dA_s dA_d$$

where θ is the angle from the surface normal and s is the distance between the source and detector. The integrals are over the areas of the source and detector. The integral can be performed under the constraint of a circular source and a circular detector, the centers of which are both on axis. The result is $$\Phi = \frac{2L(\pi r_s r_d)^2}{r_s^2 + r_d^2 + s_{sd}^2 + \sqrt{(r_s^2 + r_d^2 + s_{sd}^2)^2 - 4r_s^2 r_d^2}}$$

In this case, the specification calls for $r_d$=0.35 cm (corresponding to a 7 mm diameter aperture) and $s_{sd}$=20 cm (to maintain the $10^{-3}$ sr solid acceptance angle). The source radius is 0.65 cm. Since $s_{sd}$ is much bigger than either $r_s$ or $r_d$, we may approximate the result as $$\Phi = \frac{L(\pi r_s r_d)^2}{s_{sd}^2}$$

Evaluating this expression numerically gives 68.1 mW at the detector. A bit of a subtlety in the previous calculation is that the source radius is 0.65 cm. But the emitting area is closer to a square with side of 1.3 cm. However, the approximation is good since the corners of the square are much less bright than the center. The true illumination pattern away from the exit face of the light guide is more cross-shaped than square. This laser illumination system falls well within Class Mb specifications.

Example 2

The methods and systems of the invention can be used to validate patency of an anastomoses of the vessels supporting a flap (e.g., a deep inferior epigastric perforator flap used for breast reconstruction) and of the subdermal plexus. The flap is harvested from the abdomen, and a centrally located epigastric perforator artery and vein are skeletonized down to their source at the femoral system.

The fluorescing agent, Indocyanine Green (ICG), is reconstituted with 10 ml of sterile aqueous solvent for a concentration ranging from about 2.5 mg/ml to about 25 mg/10 ml. The ICG can be administered at this concentration through an Intravenous (IV) push through a central line by anesthesia followed by a 10 ml bolus flush of IV saline, or 2) IV push through a peripheral IV followed by a 10-30 ml bolus flush. Alternately, if the surgeon wishes to inject directly into an artery proximal the site to be imaged, the ICG should be further diluted by a factor of between about 5 and about 200. For example, 25 mg (10 ml) of ICG may be further diluted in 100 ml of IV saline. About 20-30 ml of the diluted ICG is then drawn up into a syringe with a 27 gauge needle attached. The vessel should be punctured just upstream of the area to be visualized with the needle pointing downstream, and flow should be imaged while the ICG is slowly and continuously injected.

In the case where the tissue of interest is a flap, before the flap is resected, an image is taken after administration of 5 mg (2 ml) [range=1 to 3 ml (or 2.5 to 7.5 mg)] of ICG injected IV push through either a central line or a peripheral IV to observe flow through the flap artery and vein in the adipose tissue side of the flap. This will verify that the entire flap is perfused. Preferably, the flap is a perforator flap.

A second injection of 10 mg (4 ml) [range=3 to 5 ml (or 7.5 to 12.5 mg)] of ICG with an image captured from the skin side of the flap will verify subdermal plexus perfusion out to the distal edges of the flap. Once the perforators have been resected and anastomosed to the appropriate vessels another image using 3.75 mg (1.5 ml) [range=1 to 3 ml (or 2.5 to 7.5 mg)] of ICG should be done to validate flow through the anastomoses (arterial and venous). After verification of flow through the new anastomoses has been determined, another image should be taken through the skin using 10 mg (4 ml) [range=3 to 5 ml (or 7.5 to 12.5 mg)] of ICG to verify flow throughout the subdermal plexus of the flap.

Many modifications and variations of this invention can be made without departing from its spirit and scope, as will be apparent to those skilled in the art. The specific embodiments described herein are offered by way of example only and are not meant to be limiting n any way. It is intended that the specification and examples be considered as exemplary only, with a true scope and spirit of the invention being indicated by the following claims.

What is claimed is:

1. A method of determining the patency of a vessel proximal to a tissue comprising a flap or graft, wound or burn in a subject comprising:
   a. administering a fluorescent dye to the subject;
   b. applying energy to the tissue such that the fluorescent dye fluoresces;
   c. obtaining a fluorescent image of the tissue; and d. determining from the image whether one or more vessels proximal to the tissue that comprises the flap or graft, wound, or burn is patent.

2. The method of claim 1, wherein the vessel is in the subdermal plexus.

3. The method of claim 1, wherein the fluorescent dye is a tricarbocyanine dye or an analog thereof.

4. The method of claim 1, wherein the dye is administered intravenously at a concentration ranging from about 2.5 mg/ml to about 25 mg/ml.

5. The method of claim 1, wherein the dye is administered by injection directly into an artery proximal to the tissue of interest at a concentration of about 0.025 mg/ml.

6. The method of claim 1, wherein the tissue of interest is a flap, and further comprising imaging the adipose side of the flap.

7. The method of claim 1, wherein the dye is administered less than an hour before determining patency and/or the dye is administered more than 30 seconds before determining patency.

8. The method of claim 1, wherein the image is obtained by a camera.

9. The method of claim 1, wherein energy is provided by an energy source, and further comprising modulating power output of the energy source.

10. A method of decreasing the risk of iatrogenesis during a surgical ablation procedure, comprising:
 a. administering a fluorescent dye to a subject;
 b. applying energy to heart tissue such that the fluorescent dye fluoresces;
 c. obtaining a fluorescent image of the heart tissue, wherein one or more major vessels are visible in the image;
 d. determining from the fluorescent image of the heart tissue a position of the one or more major vessels to decrease the risk of iatrogenesis during a cardiac ablation procedure; and
 e. determining where to ablate the heart based on the position of the one or more major vessels.

11. The method of claim 10, wherein step (c) is performed before the surgical ablation procedure, during the surgical ablation procedure, or after the surgical ablation procedure.

12. The method of claim 10, wherein the fluorescent dye is a tricarbocyanine dye or an analog thereof.

\* \* \* \* \*